(12) United States Patent
Yekani Motlagh

(10) Patent No.: US 10,613,069 B2
(45) Date of Patent: Apr. 7, 2020

(54) MEASURING THE PERCENTAGE OF THE FOREST COVER

(71) Applicant: Elgar Yekani Motlagh, Orumieh (IR)

(72) Inventor: Elgar Yekani Motlagh, Orumieh (IR)

( * ) Notice: Subject to any disclaimer, the term of this patent is extended or adjusted under 35 U.S.C. 154(b) by 0 days.

(21) Appl. No.: 15/853,799

(22) Filed: Dec. 24, 2017

(65) Prior Publication Data

US 2018/0188221 A1 Jul. 5, 2018

(51) Int. Cl.
*G01N 33/00* (2006.01)
*G01J 1/42* (2006.01)
*G01N 21/59* (2006.01)

(52) U.S. Cl.
CPC ........ *G01N 33/0098* (2013.01); *G01J 1/4204* (2013.01); *G01N 21/59* (2013.01); *G01J 2001/4266* (2013.01)

(58) Field of Classification Search
CPC .............. G01N 33/0098; G01N 21/59; G01N 2021/8466; G01N 21/27; G01N 21/534; G01J 1/4204; G01J 2001/4266; G01J 1/44; G01J 1/00
See application file for complete search history.

(56) References Cited

U.S. PATENT DOCUMENTS

| | | | | |
|---|---|---|---|---|
| 3,990,429 A * | 11/1976 | Mazzoni | .................. | E06B 3/677 126/712 |
| 4,282,021 A * | 8/1981 | Mazeau | .................... | C03C 4/06 501/13 |
| 4,355,896 A * | 10/1982 | Frosch | .................... | G01W 1/00 250/203.4 |
| 9,291,553 B2 * | 3/2016 | Fraley | .................. | G01N 21/359 |
| 9,297,755 B2 * | 3/2016 | Renno | .................... | B64D 15/20 |
| 9,326,348 B2 * | 4/2016 | Roshan | .................... | G01J 1/32 |
| D816,518 S * | 5/2018 | Brown | .................... | E06B 9/24 D10/46 |
| 10,012,531 B2 * | 7/2018 | Schorr | .................. | G01J 1/0266 |
| 10,234,596 B2 * | 3/2019 | Frank | .......................... | G01J 5/00 |
| 2003/0222264 A1* | 12/2003 | Matsuo | ..................... | G01J 1/42 257/80 |
| 2005/0072935 A1* | 4/2005 | Lussier | .............. | G01N 21/6456 250/458.1 |
| 2009/0000222 A1* | 1/2009 | Kalkanoglu | ............... | E04D 1/20 52/173.3 |
| 2012/0095604 A1* | 4/2012 | Alexanian | .............. | A01G 25/16 700/284 |
| 2013/0048837 A1* | 2/2013 | Pope | ...................... | G01J 1/0422 250/214.1 |

(Continued)

FOREIGN PATENT DOCUMENTS

| | | | | |
|---|---|---|---|---|
| CN | 102175653 | * | 10/2012 | ............. G01N 21/59 |
| DE | 4301177 A1 | * | 7/1994 | ............. C09K 11/59 |
| GB | 2198530 A | * | 6/1988 | ................ G01J 1/58 |

OTHER PUBLICATIONS

Espacenet English translation of foreign prior art CN-102175653.*

*Primary Examiner* — Mohamed K Amara
(74) *Attorney, Agent, or Firm* — Azadeh Saidi

(57) ABSTRACT

A device measuring a percentage of forest canopy based on a system measuring a direct radiation of sunlight and light reception. In this device, the structure of the canopy is the main base and the amount of light passing through a sensor structure and measurement of light intensity was the foundation of this invention.

3 Claims, 8 Drawing Sheets

(56) References Cited

U.S. PATENT DOCUMENTS

| | | | |
|---|---|---|---|
| 2013/0095544 A1* | 4/2013 | Berlowitz | A01G 33/00 |
| | | | 435/166 |
| 2016/0134794 A1* | 5/2016 | Grabau | G06K 9/00771 |
| | | | 348/155 |
| 2017/0096299 A1* | 4/2017 | Yang | B65F 1/1638 |
| 2017/0276542 A1* | 9/2017 | Klawuhn | G01J 1/0242 |
| 2018/0080818 A1* | 3/2018 | Tiwari | G01J 1/0219 |
| 2019/0003881 A1* | 1/2019 | Fujiwara | A61B 5/4857 |

\* cited by examiner

MEASURING THE PERCENTAGE OF THE FOREST COVER

BACKGROUND OF THE INVENTION

Measuring the percentage of forest canopy which is now an important and practical criterion because the Horizontoscope and measuring methods are not useful, by utilization of Aerial photographs which is very costly and difficult with estimation without the use of any device in most cases it is measured.

Two main methods to measure the percentage of forest canopy are as follows:
1. It is supplied by the device called Horizontoscope that according to the image it took from the canopy and the space crown of trees had been analyzed by the software in the office with the number of canopies. By Horizontoscope's method, it's very time-consuming and do not perform in the forest and necessary facilities are not available for analysis. Also, it doesn't immediately get provided to the expert.
2. It is determined by Visual approach and using people's experience and skillful experts due to the density and estimated shortness canopy, that is just based on experience and information that has emerged over time. The visual approach is not accurate, not everyone can use this method because there is no sufficient knowledge and experience to do it and different teachers got different numbers and there is a possibility of error.
3. Aerial photos method because of being costly and lack of access speed and specialty was not useful. Now, the device has been fixed all the defects of the methods such as heaviness, cost, low speed and lack of access and the public's understanding of the method of calculation.

SUMMARY OF INVENTION

This device is built on a simple electronic system based on the values obtained from the environment acquires the Forest Canopy quantity. This device receives the environment light as a raw value and after processing (FIG. 1), the intensity of ambient light is achieved by candle (LUX) and light intensity in the predefined range of 0-1000 LUX by applying a conversion formula the value of forest canopy acquires.

In fact, the simplicity of the device is an advantage to better understand the function in the jungle. The original plan was evaluated in several stages. On the base, the device measuring the percentage of forest consisted of several pieces of sensor (5) LDR with high sensitivity that was chosen after several reviews of sensor (5) Congruent with forest. The device is built based on the lux meter system were implemented (With a plurality of sensor segments (5) and light intensity changes).

The empty space (an area of empty space) changes the intensity of light passing through space. The initial hypothesis with circuit design to receive light intensity was confirmed since photometry in the forest and determination of canopy values of trees in ecology is very important in executive and research programs, Also, according to the estimation of light and quantifying it will reduce the possibility of mistakes by different people, the absence of a specific technology and applications for the accurate measurement of this important standard was the main reason for the construction of this device.

The amount of light passing through and comparing it with the light source was the original idea of building this device. The hypothesis of canopy blocks direct light into the forest and amount or intensities of light reaching the forest floor With canopy density have reversed ratio, that is to say, more the light reaching the forest floor is less dense canopy, it is the foundation of building this device.

As we regard the amount of light emitted in the forest, which is in the upper space of the canopy, a fraction of this amount has passed the dense of the canopy and reaches directly to the forest floor according to this I was initially given a formula.

Density amount of canopy=Direct light transmitted through canopy to forest floor/total sunlight volume above forest canopy Wherein the total sunlight volume is measured at any time of the day or weather, when the forest canopy is being calculated and the device is being calibrated.

Then a circuit was designed and built to achieve the above formula.

DETAILED DESCRIPTION

Direct light beam passing through the empty space of canopy that reaches the floor was the basis of this device. The intensity of the light varies due to the density of the canopy that by processing the variation we can reach the idea of building this device.

Figure 1:
FIG. 1, shows radiation of sunlight Between the branches of trees

In FIG. 1, light beam passes through the empty space of canopy and reaches the floor.

The direct transmission of light that reaches the Earth's surface from empty space of canopy based on the FIG. 1 represents a huge amount of canopy and empty space. It means the light beam passing through the sensor directly to the surface of the sensor which measures and uses a funnel-shaped sensor section (5) only receives direct light. Sensor (5) is sensitive to light intensity. Wherein light intensity as raw data becomes available to us, LUX light intensity is determined, according to the programming that was done raw numbers LUX light intensity was converted to percentage. In fact, the circuit lux meter is used to measure light intensity. According to the available information in the sources, the light intensity is approximate between 0-1000 LUX. In circumstances of space that there are no traces of trees canopy and Sunlight naturally reaches to the surface of the sensor section (5).

In the area of free space different lights were glowing on the device surface, so the Programming was done. If there are no canopy and there is no trace of leaf and crown of trees, and all the intensity of sunlight without any obstacles reaches the sensor surface, light intensity was MAX 1000 lux, so with no obstacle the programming was done.

Figure 2:
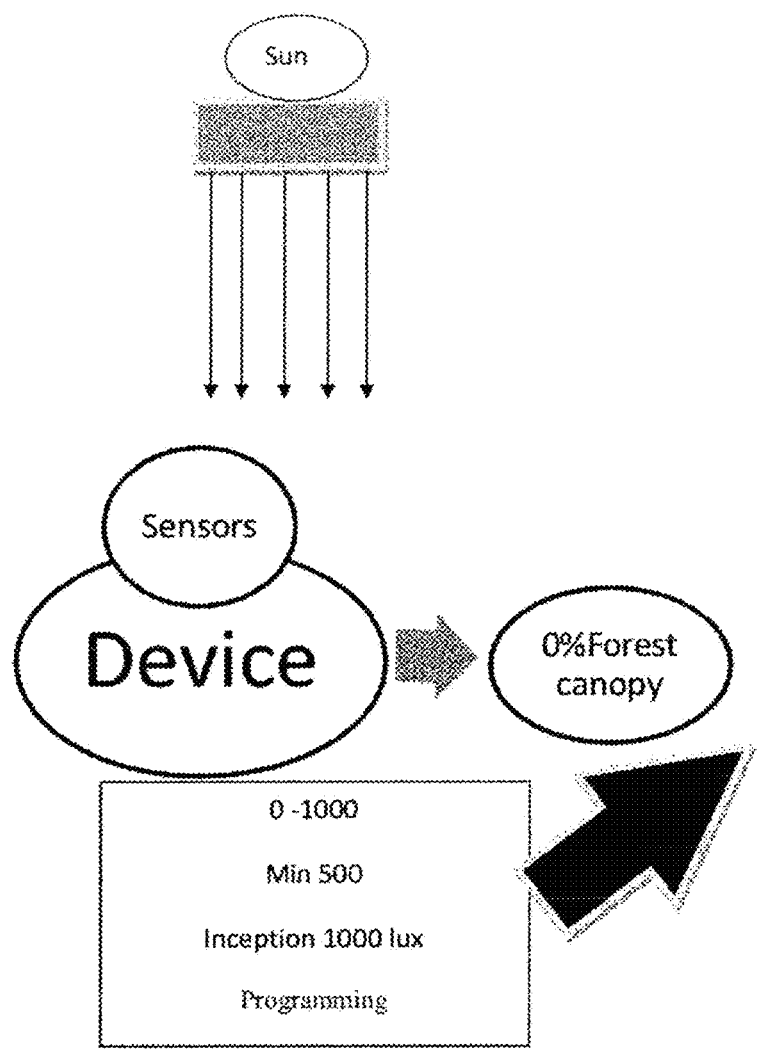
FIG. 2, displays the diagram of where the percentage of forest canopy is 0%

If there is no obstacle and light intensity fully get to the sensor surface piece (5), percentage of forest canopy is 0% (FIG. 2). In the next state by simulation and in circumstances with obstacle and almost no light beam reaches to the sensor surface piece (5) and light intensity written on the sensor surface piece (5) is 0 LUX.

Because of the extremely large canopy light barrier the light reaching the sensor surface piece (5) is determined by programming. That if the canopy is very dense, there is no light on the sensor surface piece (5), therefore receives only directly transmitted light and the percentage of forest canopy will be placed 100%.

Figure 3:
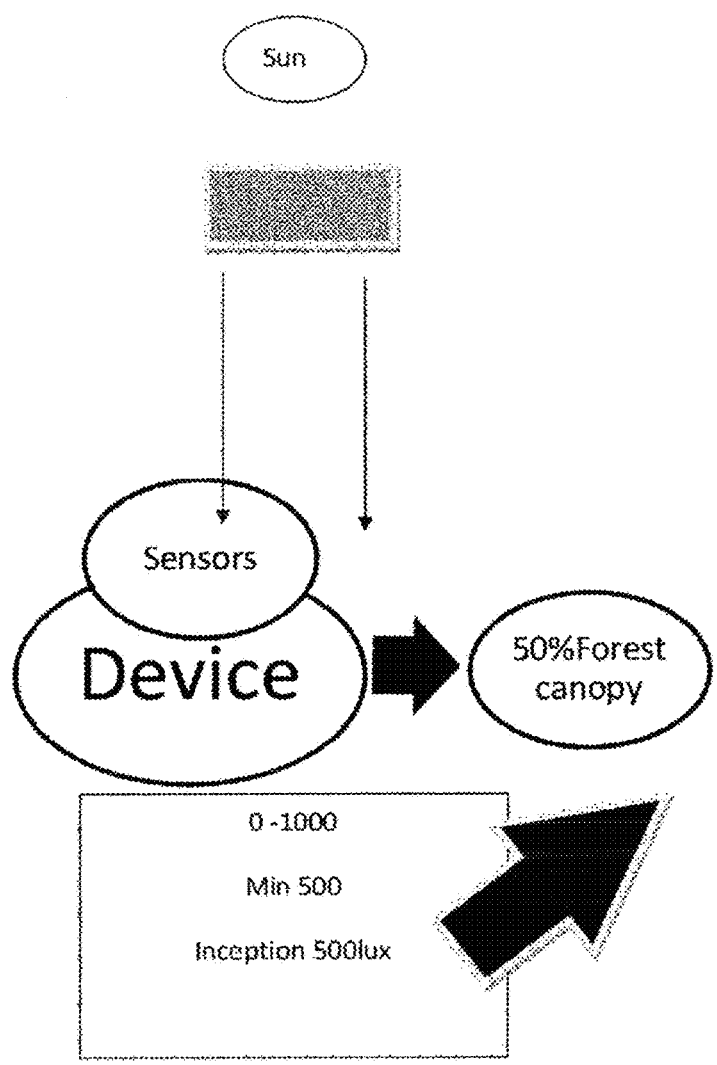
FIG. 3, displays the diagram of where the percentage of forest canopy is 50%
Figure 4:
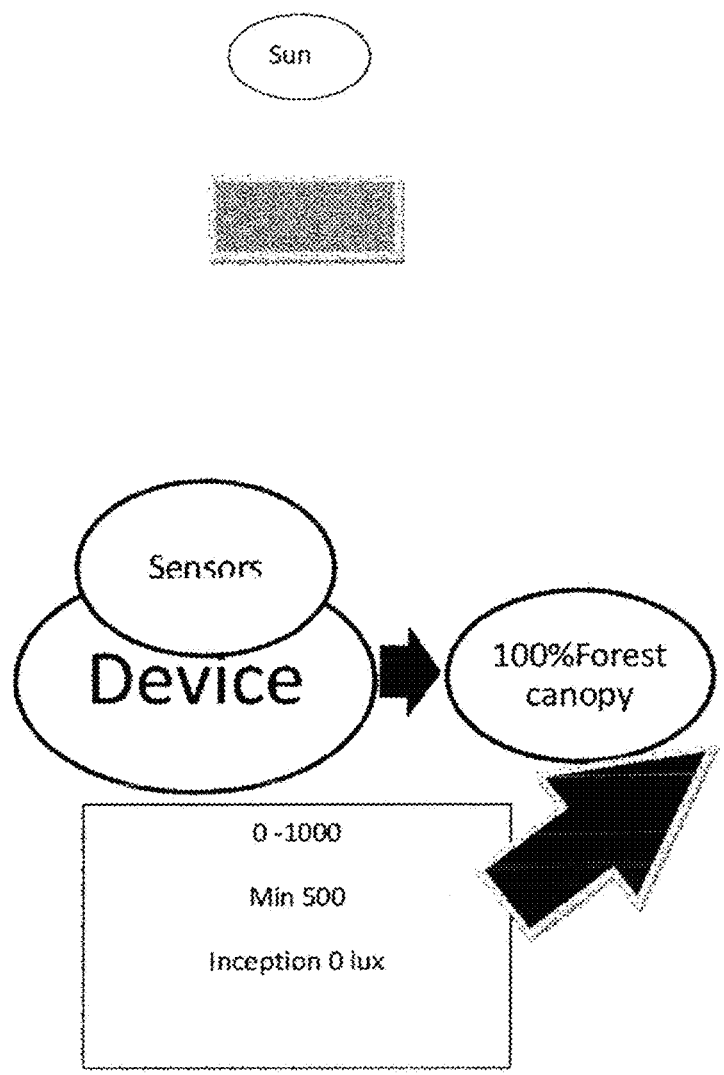
FIG. 4, displays the diagram of where the percentage of forest canopy is 100%
Figure 5:
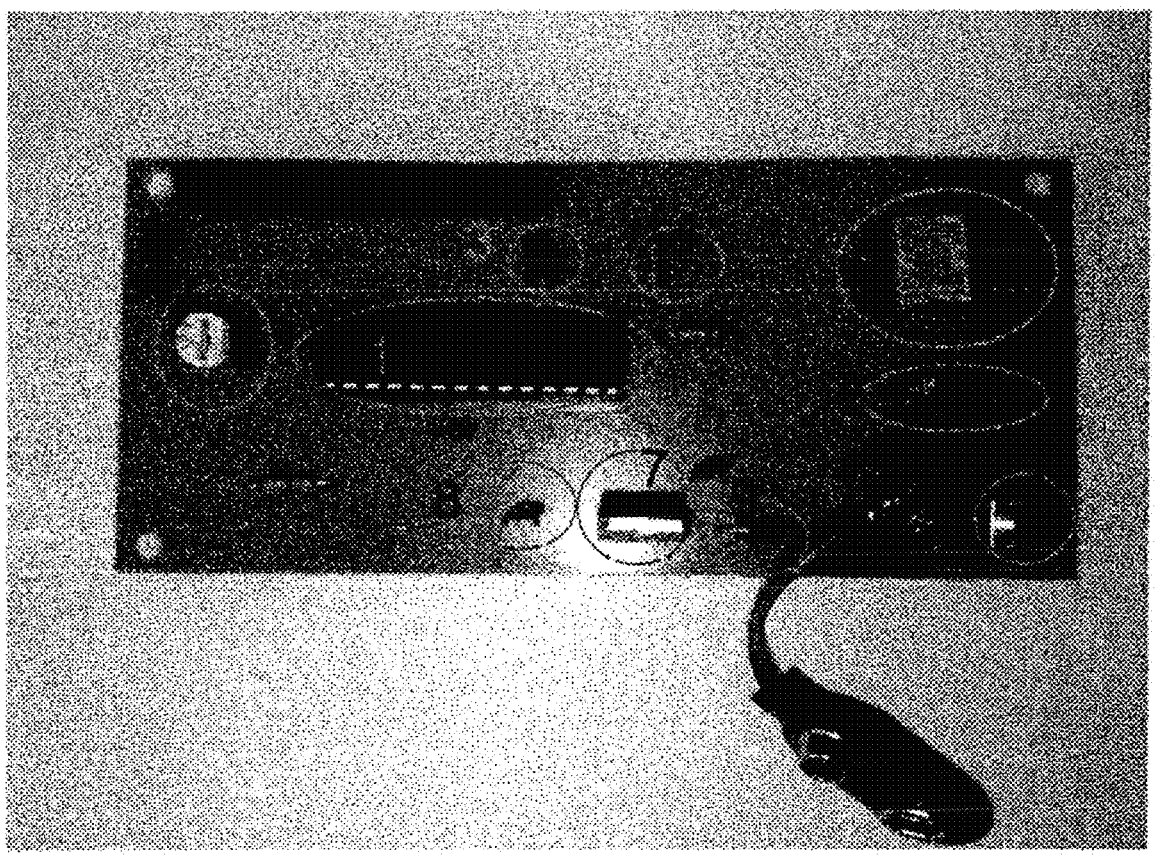
FIG. 5 represents the electronic components used in this device

Between 2 numbers 0-1000 LUX varied light intensity was spun to the machine surface, to do the ranging and determination. If the amount of light hitting the sensor surface piece (5) at 50% is 1000 LUX, it means 500 LUX and therefore the canopy cover is 50% (FIG. 3).

The operation was conducted in the light intensity varies in different situations, And ranging % canopy and programming were determined. It is very accurate for this reason the sensor (5) only receives direct light through the empty canopy space. Measurement of the forest is plot. That is, except for research and protection of forest conditions is divided to be systematic and given the extent of forest plot in the same size will be created.

In the original sample after it was given to the factories it is made of several major pieces like a network scattered in plots (One piece of the major components were built and tested) with coordination the extent of coverage based on the space is determined, transfers to the main processor one-to-one. The processor then analyzes the average canopy cover in the sample, and gives to the expert the final result. In this way, in the shortest time parts of the canopy cover is determined. In each of the major components such as multi-sensor device (5) with respect to the extent of the plot is placed in an orbit to cover all the plots. In fact, the main device can be made by separating and connecting several pieces. For the proper functioning of the device in different environmental conditions such as cloudy, sunny, day, latitude and different seasons a complementary circuit is used so that the device is exposed to direct sunlight light source and there isn't any obstacle between the light source and the completed device.

Direct light intensity received from outside of the forest sets and becomes forest-based computing devices. The main unit also changes with the change of supplementation circuit. Data on the circuit transfer to the main unit every second so the basis of calculating the main unit at any time gets updated by the supplementary device and cover in various environmental conditions are provided in details. Using the main device in the forest and a supplementary device outside the forest canopy cover in any environment precisely and scientifically is measured and given to the expert to be used in various processing in accordance with the defined requirements of forest and expert. Canopy cover in forestry projects is an important decision the proper functioning of the system will help forest experts to reach a correct decision.

In other methods standard of measuring forest cover percentage in an office environment can be achieved after analysis, but device canopy cover criteria are obtained in less time and with the simplest method. Another innovation is a lightweight and portable machine in the harsh conditions of the jungle that can be used to assess the extent of forest and samples and majors used to select the required components and measure. Due to the easy and understandable idea of this device, it is obtained by using the sunlight to the forest, so the original device is less expensive than devices and sophisticated methods to measure the percentage of the forest canopy.

The list of all the components used in the circuitry of the present invention:
1 Microcontroller
2 Potentiometer
3 Transistor
4 Resistance
5 Sensor
6 Potentiometer LDR
7 Voltage converter
8 Diode
9 Capacitance lens
10 Button to activate the backlight

DETAILED DESCRIPTION OF THE DEVICE

The initiative of this device combined with the use of luxurious meters of natural elements (sun) to determine the percentage of the forest canopy and built with the combination of scientific principles and new ideas of this device. This device is capable of changing in research and practical circumstances.

Due to the size of plots in the original sample, we can enter small major like components to the circuit or connect to the main unit, until in a circular, rectangular, square sample piece intensity of light reaching the forest floor, and as a result, the forest cover percentage was calculated, so the flexibility of this device changes in accordance with the forest conditions which is functional to the researchers.

It is very simple and easy to use and requires no prior training for employees and managers a simple system inspired by nature is understandable to all people. Changing ability of the style in a device with expected shapes of the original sample according to its use in sample pieces and to determine the percentage of plots in the forest canopy or necessarily using completed device without the use of resolution ability to determine the overall forest canopy has the ability to perform.

The basis of this system is based on the hypothesis canopy blocking direct light into the forest stand and amount or the light intensity reaching to the forest floor is inversely proportional to canopy density, it means, more the light reaching the forest floor less is the canopy density so this hypothesis is reconstructed in the form of a device. The purpose is the occupied surface of the canopy percentage ratio of canopy trees on the ground to the desired level.

If all the forest surface is occupied by the image of the canopy of trees and, in fact, there is no empty space to pass through the forest and reach the surface, the cover will be 100%. So it is called canopy closure or complete, If the amount of light reaching the forest floor is the outdoor condition the canopy percent would be 0 and not to open the canopy.

The importance of canopy cover and percentage, includes the following:
Increase soil quality, soil fertility, crop protection, temperature setting revitalization, the nature of species, forest type and length and diameter of growth The significance of this device is that the production forest is under operation, the canopy must be closed and compact until breeding has not started and opening of the canopy before revitalization to the total growth and forest tree quality and growth quality and using the incidence rate of the device is placed in the hands of forest expert that can adopt the decision.

Cover set ➔ The effect of light in the forest

The importance of this device and the percentage cover obtained by the device to use in the research and planning cases to improve the quality of forest regeneration and reforestation and forest improvement in several measures of happiness and applications the standard obtained from this device is the basis of programming in the forest by the engineers. The device is capable to get canopy cover criteria by combining an approved scientific principle and using a metering circuit in a simple, intuitive and functional way.

Forest canopy and the sun are the cause and effect on each other in the forest environment using sunlight has given a scientific and accurate basis for calculating the percentage of forest cover to researchers. The forest canopy changes the amount of light reaching the forest floor. Forest researchers measured the intensity of light in the forest, but the idea of understanding to use the intensity of light reaching the forest floor to canopy cover is from the innovation and functionality of the device. The idea of combining the intensity of light Survey (LUX METER) and canopy poll, simply merged in this device to give researchers and managers the amount of canopy cover in the fastest time and most flexible system.

The purpose of building this device is to substitute and use it instead of visual estimation that is invalid and unscientific and reaching the criteria of the canopy in the shortest time and simplest method and using forest conditions to determine the important criteria of the forest. Another goal of making the device is the production of inexpensive and portable generators in the steep and rugged forest.

For operating on the device and flexible conditions major like pieces that are connected together, all the output data get processed at once. To do this, we can use a Microcontroller of output data to receive all Microcontrollers and operation such as averaging and so can be done on all the data at once.

Figure 6:
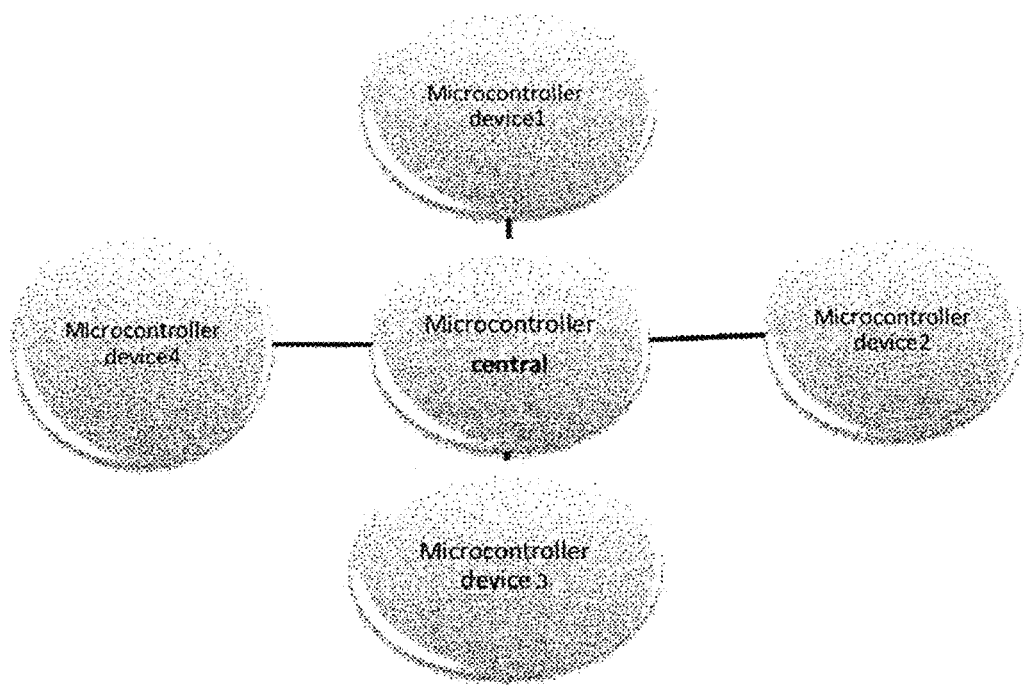
FIG. 6, displays the micro controlling unit
Figure 7:
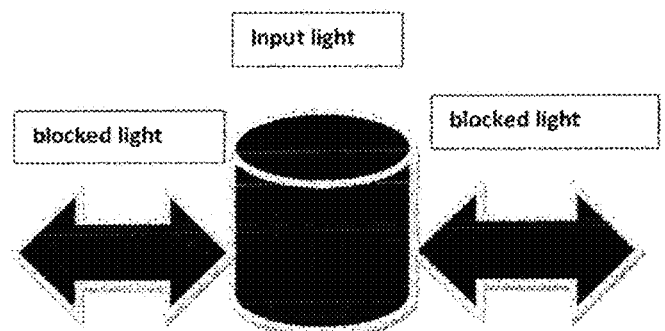
FIG. 7, displays a block diagram of the input light
Figure 8:
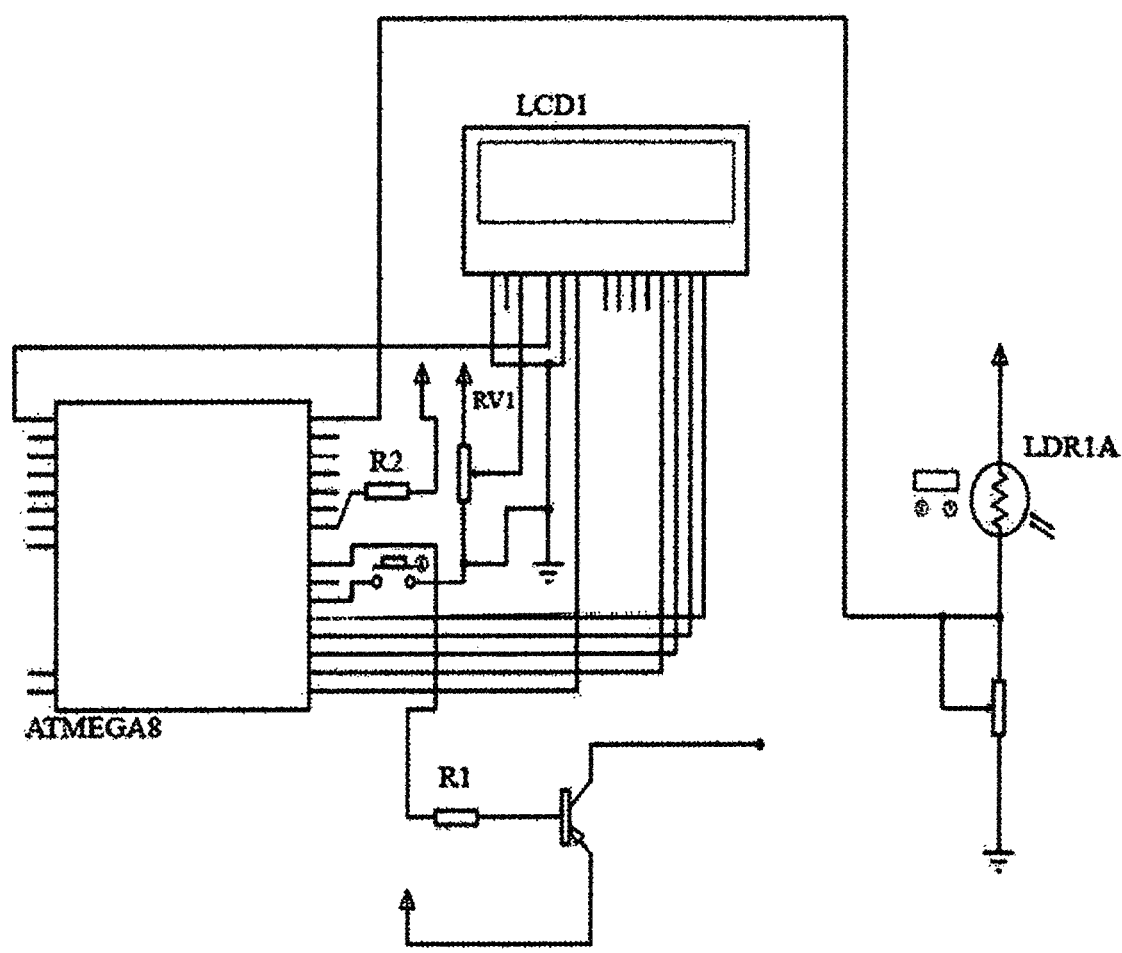
FIG. 8, displays The LUX METER circuit used in the device
Figure 9:
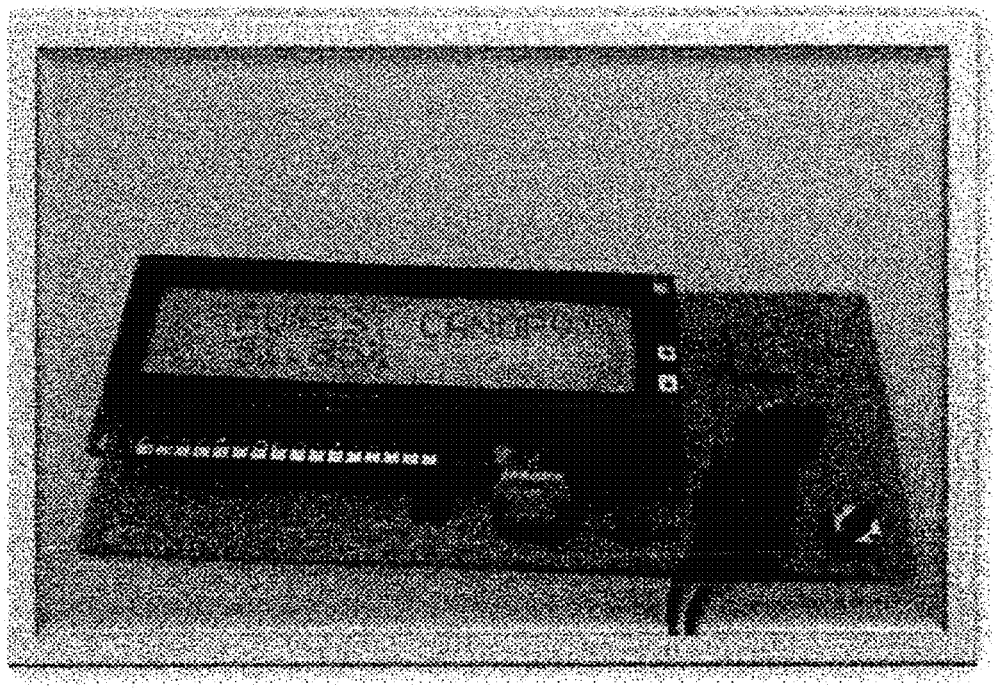
FIG. 9, displays a reading of the forest percentage coverage device

This is effective and easy to use a method that uses I/O Microcontroller features. This way is applicable both wired and wireless FIG. 6 (wireless).

Use of the physical environment on the sensor device (5) in the form of a cone or any other form limits the light on the LDR (depending on the shape of the object). For the sensor device (5), to calculate only light that shines perpendicular to the ground, In this case, by inserting a cylindrical object that the sensor just calculates the Transmitted light beam from the empty space of canopy (the object should have a size and height not to impact the sensor device (5) and the ambient light does not affect the result.

The Material is made of light insulation plastic and metal objects are good choices for most environments. it is proved that the calculated light intensity after installation with light won't be the same before installation, cause the radiation that shine with less angle of LDR now got blocked after inserting the object. It is also possible not to use the cylindrical object for limited broken light and ambient light by measuring the ambient light intensity and the intensity of the transmitted light and the broken pieces and programming in device prevent sensor values (5). In this device, all the cases that make a flaw in test results surveyed to get a perfect solution.

Electrical Specifications:

The data input of this device (light) receives through an optical sensor (LDR) piece (5) and sent to the processor.

LDR optical sensors can be found in different sizes that in the example of an LDR a mega-ohm device that can be used depending on the type and use of other samples. When the light shines on LDR its electrical resistance change, therefore the potential difference across it will also change. One of the LDR bases is connected to the voltage source and the other one to the input analog to digital Microcontroller (ADCO). Thus, by changing the light intensity directly, the base electric potential of the analog to digital Microcontroller also alters.

Various Microcontrollers can be used in this invention. BASIC programming language is used in this device, so, after operations on information the result is sent to display on the LCD screen.

The device has a 2×16 character LCD display, which is used by the bases of port D the Microcontroller to be launched. Both energy supply and the lack of impact on the functioning of the display light optical sensor, backlight display by one of the foundations of the Microcontroller (PORTD2) and a key in both cases is designed to selectively turn on or off. If necessary, you can also take advantage of other available samples on the market.

Power supply: the power of the device from a circuit consists of three elements, diodes, voltage converter-regulator (1) and batteries. Also for the protection of circuit against negative voltage Used which may arise as a result of the reverse battery of a diode (1). The device is made of LDR voltage signals that get into the Microcontroller and the amount of light intensity are processed by a single candle (LUX). The user must ensure correct implementation of the values given by real values.

For example, if the input voltage signal to the Microcontroller in the range of 0.2 V to be considered as a single candle, the circuit must be calibrated so that for optical radiation measurement unit plugs into the LDR, a voltage signal in the range of 0.2 volts of LDR out into the Microcontroller's ADC base. For this purpose, putting a series variable resistor (RV2) with LDR allows calibration circuit. You can also measure the intensity of sunlight at different times and program the information in Microcontroller to calculate the amounts Forest Canopy and thus the overall circuit and the machine were designed and built.

The limitations of this device (the bulk of these limitations by using supplements out of the jungle in different environmental conditions, such as cloudy, sunny, day, latitude and different seasons use a complementary circuit) are the light. It is recommended for the proper functioning of the device and determining the exact measure of the percentage of forest canopy in perfect lighting conditions and perfect weather and all measurements, to be done at a time. During the construction of the main unit, for the same function in all weather conditions instead of circuit devices supplement uses a correction coefficient that measures the intensity of sunlight at different times and program the information on the Microcontroller, till at all times of the day calculate the values of the Forest Canopy and the Microcontroller to be programmed to calculate measurements more accurate and unrestricted.

Advantage: the results are fast and in the forest environment, they are easy to use and understandable for all users of the forest. Using a proven scientific method in the device, making the device based on the concept of the cover and the use of performance in canopy cover measurement

The invention claimed is:

1. A forest canopy percentage (FCP) measuring method comprising the steps of:
    a) Placing a light measuring device under direct sunlight at a first location outside of a chosen forest at an area without any trees or light blocking obstacles;

b) Covering at least one LDR (light dependent resistor) sensor of said light measuring device with a covering device having a specific shape and height, made of light blocking material; therefore allowing only direct and unfiltered sunlight beams through and directed/transmitted on said at least one LDR sensor and blocking any other radiated or indirect light from reaching said at least one LDR sensor;

c) Measuring said direct sunlight beams passing through said covering device, reaching said at least one LDR sensor at said first location, d) Calculating a first light intensity value in LUX unit, based on readings of said at least one LDR sensor and preprogramming said light measuring device at a MAX light intensity value of 1000 LUX based on said measured and calculated LUX unit;

e) Setting and preprogramming a value for MIN percentage of forest canopy to 0%, corresponding to said MAX intensity of 1000 LUX;

f) Placing said light measuring device at a second location which has a thick canopy of trees and is a fully covered area of said chosen forest wherein no direct sunlight passes through said thick canopy;

g) Recording and calculating any readings of said at least one LDR sensor as a second light intensity value in LUX unit at said second location;

h) Preprogramming said light measuring device at a MIN light intensity value of 0 LUX based on said measured second light intensity value;

i) Setting and preprogramming a value for a MAX percentage of forest canopy to 100%, corresponding to said MIN intensity of 0 LUX;

j) Programming a light intensity range for said light measuring device between said MIN and MAX LUX values of 0 to 1000 and setting canopy percentage range based on said light intensity range, wherein said light intensity range is inversely proportional to said canopy percentage range;

k) Placing said light measuring device at any desired location in said chosen forest;

l) determining a forest percentage coverage based on said direct sunlight passing through said covering device and measured by said at least one LDR sensor at said desired location;

m) displaying said percentage coverage on an LCD screen of said light measuring device as said FCP for said chosen forest; and n) wherein steps a through m are performed in the recited order.

2. The method of claim 1, wherein said specific shape comprises a cone, funnel and/or cylindrical shape; and wherein said light blocking material comprises light insulation plastic and/or metal and wherein said covering device has a height directing only perpendicular lights to said at least one sensor.

3. The method of claim 2, wherein a density of said chosen forest at said desired location is calculated by:

Density amount of canopy=light transmitted through canopy to forest floor/total sunlight volume above forest canopy; wherein said total sunlight volume is measured at any time of the day or weather at said first location.

* * * * *